United States Patent
Andrus

(10) Patent No.: US 9,821,101 B2
(45) Date of Patent: Nov. 21, 2017

(54) CARDIAC PUMP IMPLANTATION DEVICE AND METHOD

(71) Applicant: HeartWare, Inc., Miami Lakes, FL (US)

(72) Inventor: Lance Lynn Andrus, Southborough, MA (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 14/962,511

(22) Filed: Dec. 8, 2015

(65) Prior Publication Data

US 2016/0166746 A1 Jun. 16, 2016

Related U.S. Application Data

(60) Provisional application No. 62/089,910, filed on Dec. 10, 2014.

(51) Int. Cl.
| | |
|---|---|
| *A61M 1/12* | (2006.01) |
| *A61M 1/10* | (2006.01) |
| *A61B 17/32* | (2006.01) |

(52) U.S. Cl.
CPC ............. *A61M 1/122* (2014.02); *A61B 17/32* (2013.01); *A61M 1/1008* (2014.02)

(58) Field of Classification Search
CPC .. A61M 1/122; A61M 1/1008; A61M 1/1087; A61M 1/1089
See application file for complete search history.

(56) References Cited

U.S. PATENT DOCUMENTS

| | | | |
|---|---|---|---|
| 6,802,806 B2 | 10/2004 | McCarthy et al. | |
| 7,942,805 B2 | 5/2011 | Shambaugh, Jr. | |
| 8,343,028 B2 | 1/2013 | Gregoric et al. | |
| 2007/0167968 A1 | 7/2007 | Pandey | |
| 2007/0167969 A1 | 7/2007 | Pandey | |
| 2011/0251450 A1 | 10/2011 | Pagani et al. | |
| 2012/0010455 A1* | 1/2012 | Reichenbach | A61M 1/10 600/16 |
| 2012/0059212 A1 | 3/2012 | LaRose et al. | |
| 2013/0041460 A1 | 2/2013 | Heilman et al. | |
| 2013/0150654 A1 | 6/2013 | Stanfield et al. | |

\* cited by examiner

*Primary Examiner* — George Evanisko
(74) *Attorney, Agent, or Firm* — Christopher & Weisberg, P.A.

(57) ABSTRACT

A system and method for implanting a ventricular assist device ("VAD") within the heart includes one or more tools, each having a body with a passage. Each tool body can be engaged with an anchor ring assembly secured to the heart. A coring tool can be advanced through the passage in a tool body and used to from a hole in the heart wall, and then valve actuating elements carried on the tool can be used to close a valve incorporated in the anchor ring assembly. A VAD can be passed into the heart through a passage in a tool body after opening the valve. The procedure can be performed while the heart continues to beat, without gross blood loss.

17 Claims, 6 Drawing Sheets

CARDIAC PUMP IMPLANTATION DEVICE AND METHOD

CROSS-REFERENCE TO RELATED APPLICATIONS

This application claims the benefit of the filing date of U.S. Provisional Patent Application No. 62/089,910, filed Dec. 10, 2014, the disclosure of which is hereby incorporated herein by reference.

BACKGROUND OF THE INVENTION

The present invention relates to devices and methods for installing pumps or other devices within the heart of a patient.

Ventricular assist devices ("VAD") are used to assist the heart of a patient suffering from heart failure. A VAD includes a pump having an inlet and an outlet. The pump is installed within the body of the patient, with the inlet of the pump communicating with a vein of the patient and with the outlet of the pump communicating with an artery. For example, where a VAD is used to assist the left ventricle of the heart, the inlet of the pump is in communication with the left ventricle, whereas the outlet is in communication with the aorta.

As described, for example, in U.S. Patent Application Publication No. 2009/0203957, the disclosure of which is hereby incorporated by reference herein, it has been proposed to mount a VAD with the housing of the pump disposed inside the heart. The pump may have an inlet at a proximal end of the housing and an outlet at a distal end of the housing. An outlet tube is connected to the distal end of the housing and projects through a valve of the heart into the appropriate artery. For example, where the VAD is used to assist the left ventricle, the outlet tube projects through the aortic valve into the aorta, so that the outlet of the pump is in communication with the aorta.

As described in the aforementioned patent publication, the housing of the pump may be connected by an elongated member to a proximal housing remote from the pump. Electrical connections extend through the elongated member from the proximal housing for connection to a controller and power source. In use, a device known as a sewing ring is fastened in place on the exterior of the heart. The sewing ring has a bore extending through it. The surgeon fastens the sewing ring in place on the exterior of the heart, typically at the apex of the heart. The surgeon makes a hole in the wall of the heart inside the bore of the sewing ring. The device is advanced through the bore and the hole in a distal direction, with the outlet tube and pump housing leading and with the proximal housing trailing.

The pump is advanced in this way until the pump is positioned with the outlet cannula projecting through the valve, and with the proximal housing disposed inside the sewing ring and projecting out of the exterior of the heart. A clamp associated with the sewing ring is then tightened so as to secure the proximal housing of the pump to the sewing ring, and thus fasten the pump in place in the heart. It is desirable to install such a pump without arresting the heart beat and without the use of a cardiopulmonary bypass machine. In such a procedure, commonly referred to as an "off-pump" procedure, the surgeon must form the hole and install the pump in the heart while the heart continues beating. As the heart beats, it tends to forcefully expel blood through the hole. Moreover, the pump should be introduced into the heart without also introducing a bolus of air into the interior of the heart. While a skillful surgeon can successfully perform an off-pump installation of such a pump without fatal blood loss or air embolism, further improvements would be desirable.

BRIEF SUMMARY OF THE INVENTION

One aspect of the invention provides systems for installation of a ventricular assist device. A system according to this aspect of the invention desirably includes an anchor ring assembly. The anchor ring assembly may include an anchor ring adapted for fastening to the wall of the heart. The anchor ring assembly desirably defines a bore having proximal and distal ends, the distal end of the bore facing toward the wall of the heart when the anchor ring is fastened to the wall of the heart. The anchor ring assembly may further include one or more valve elements movable between a closed position in which the one or more valve elements substantially occlude the bore and an open position in which the one or more valve elements do not substantially occlude the bore.

The system preferably includes at least one tool. Each tool desirably includes a tool body having proximal and distal ends, a proximal-to-distal axis extending therebetween, and a passage extending between the ends of the body along the proximal to distal axis. Preferably, the distal end of the body is adapted to releasably engage the anchor ring assembly so that the passage communicates with the bore in the anchor ring assembly. Each tool desirably includes one or more valve actuating elements movably mounted to the body, the valve actuating elements being mechanically linked to the valve elements when the body is engaged with the anchor ring assembly. The tool desirably also includes a control element operatively connected to the valve actuating elements so that the valve elements can be moved between the open and closed positions by actuating the control element, at least a part of the control element being disposed remote from the distal end of the body.

A further aspect of the invention provides methods of installing at least part of a ventricular assist device. A method according to this aspect of the invention desirably includes the steps of providing an anchor ring assembly on the wall of the heart, and forming a hole through the wall of the heart so that a bore in the anchor ring assembly communicates with the hole. The method preferably further includes the steps of occluding the bore and connecting an installation tool to the anchor ring assembly so that a passage in the installation tool communicates with the bore in the anchor ring assembly adjacent a distal end of the installation tool. The method preferably also includes the step of inserting a component of a ventricular assist device into the passage of the installation tool and filling the passage with a liquid so that the liquid displaces air from around the component. The method preferably also includes the step of removing the occlusion from the bore and, while maintaining liquid around the component, advancing the component through the bore and passage at least partially into the heart so that the component occludes the bore. The method may further include the steps of securing the component in place and removing the installation tool.

Figure 1:
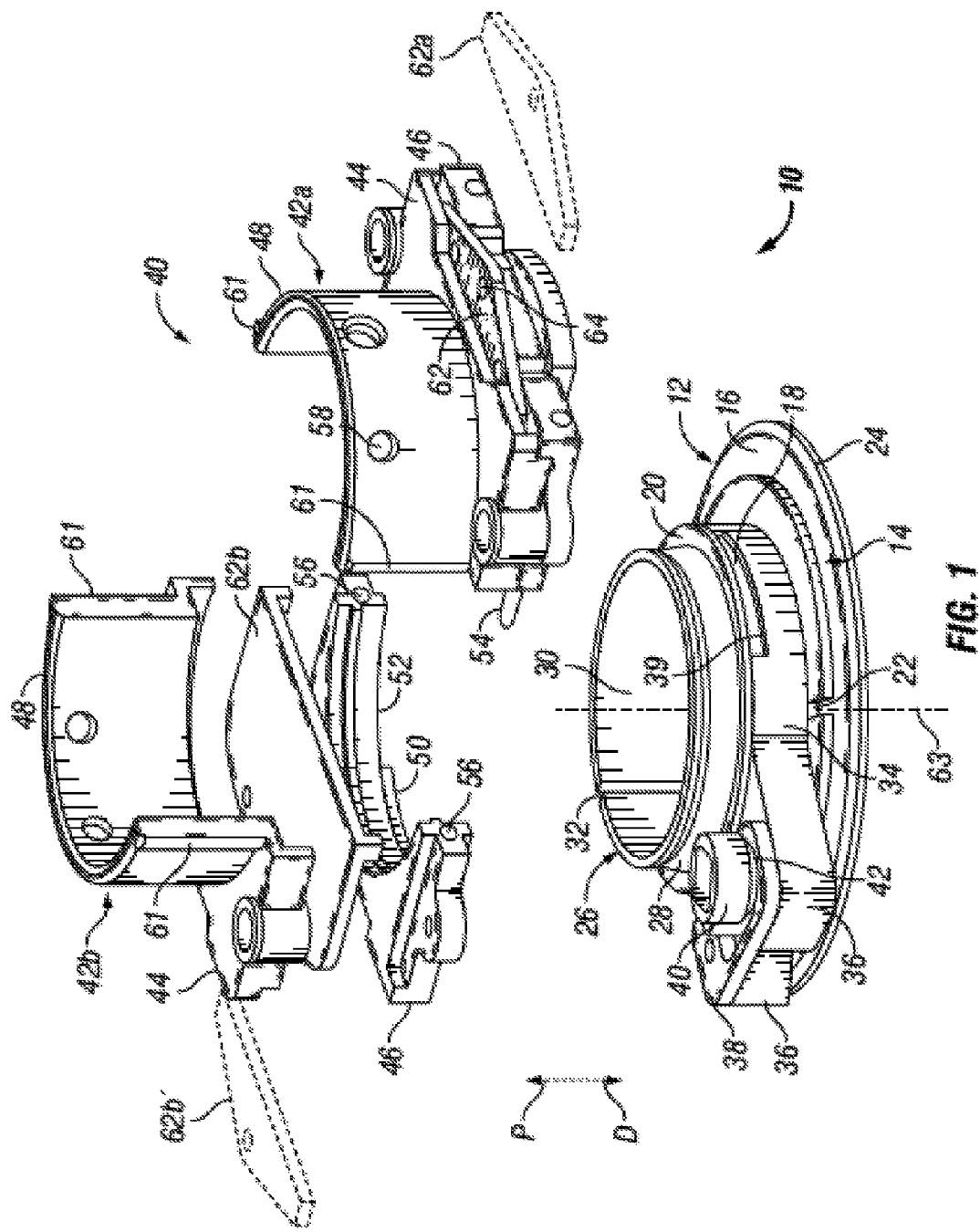
FIG. 1 is a partially exploded perspective view depicting certain components used in a system according to one embodiment of the invention.
Figure 2:
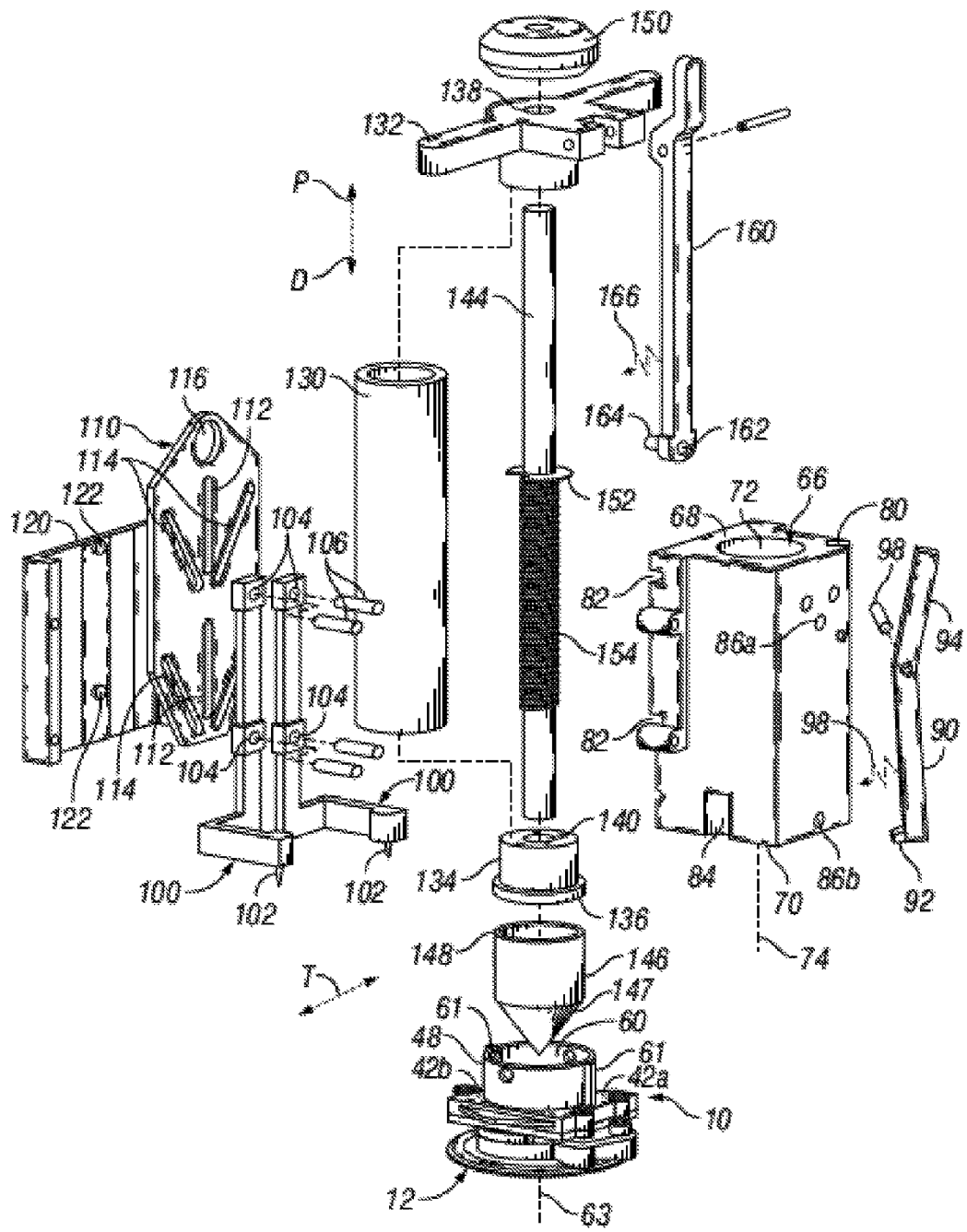
Figure 3:
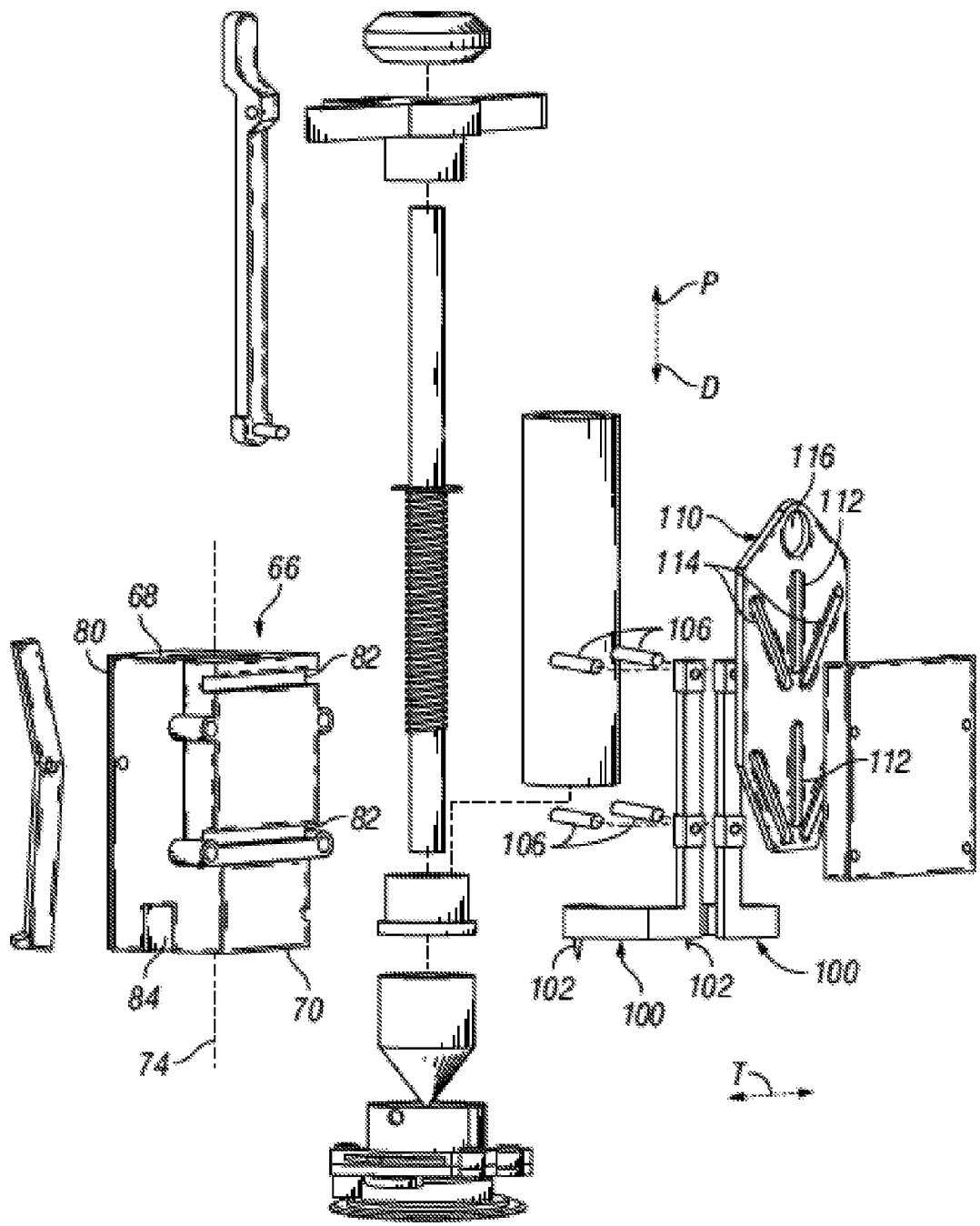

Each of FIGS. 2 and 3 is a partially exploded perspective view depicting the components of FIG. 1 in conjunction with additional components of the system.

Figure 4:
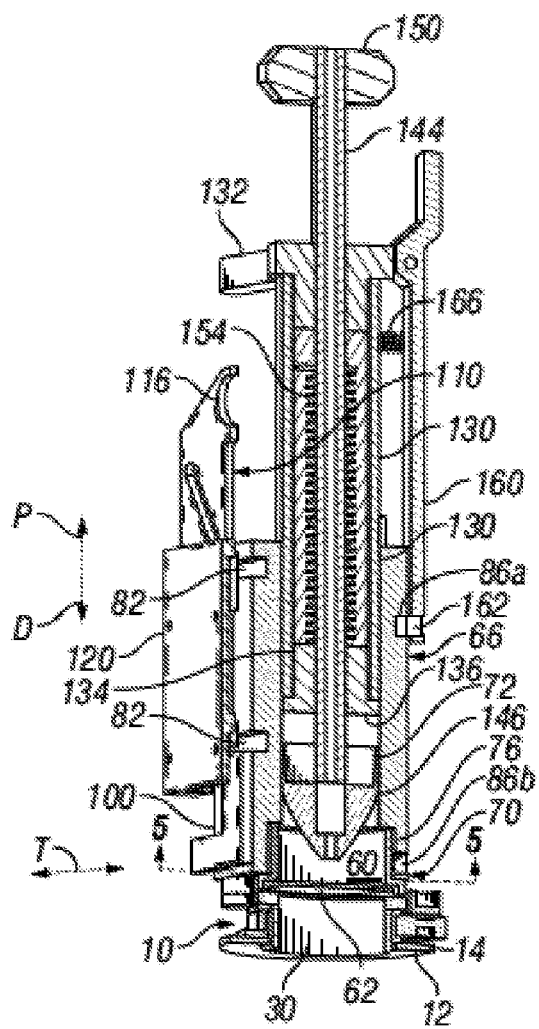

FIG. 4 is a cut-away perspective view depicting the components shown in FIGS. 2 and 3 in an assembled condition during one phase of operation.

Figure 5:
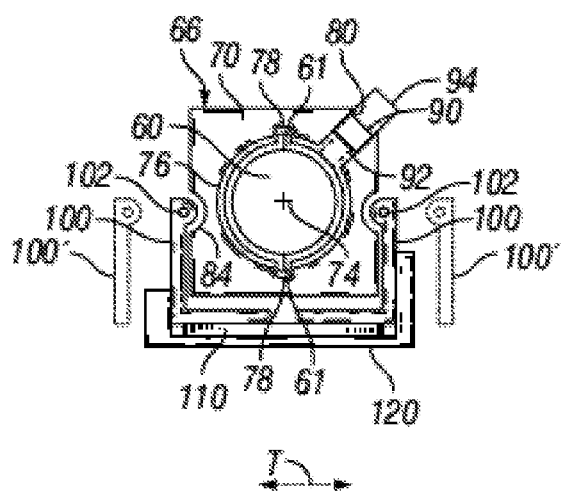

FIG. 5 is a sectional view taken along line 5-5 in FIG. 4.

Figure 6:
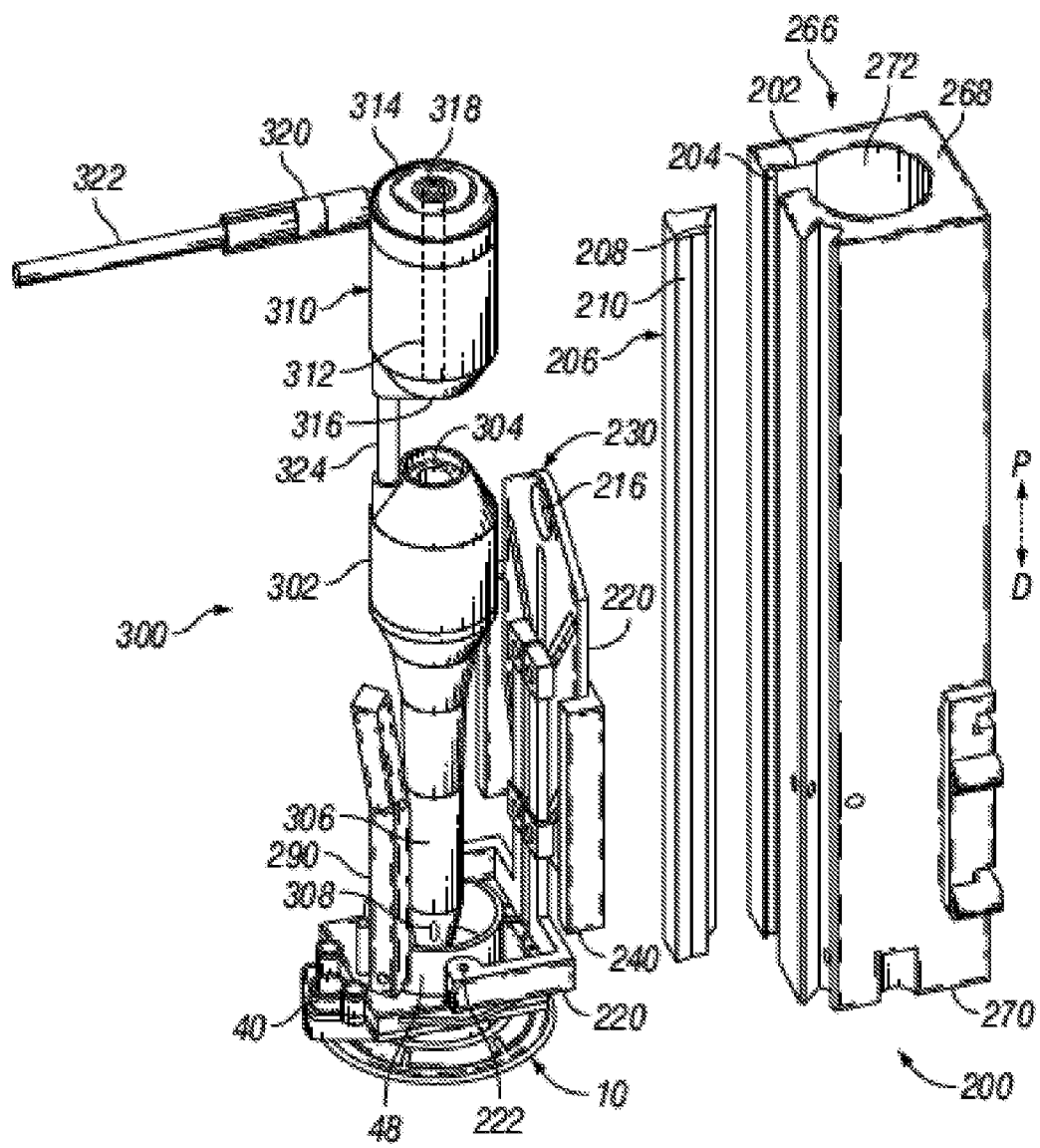

FIG. 6 is a perspective, partially exploded view depicting additional components used in the system of FIGS. 1-5.

Figure 7:
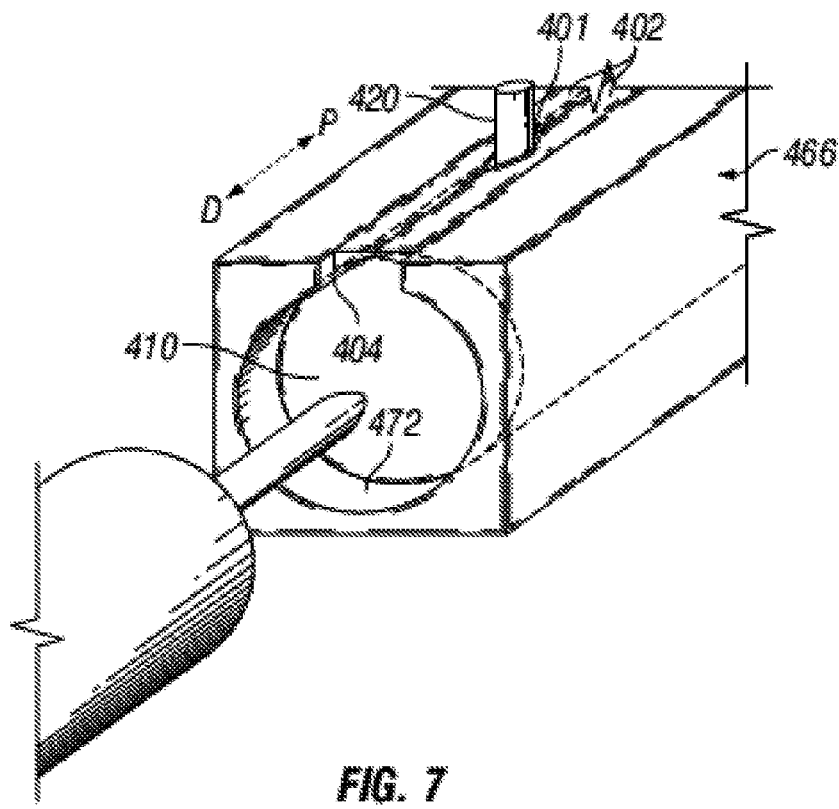

FIG. 7 is a fragmentary, diagrammatic perspective view depicting certain elements of a system according to a further embodiment of the invention.

Figure 8:
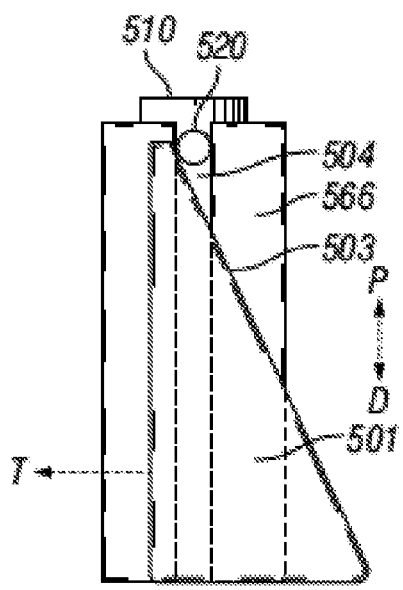

FIG. 8 is a diagrammatic plan view depicting certain elements of a system according to another embodiment of the invention.

Figure 9:
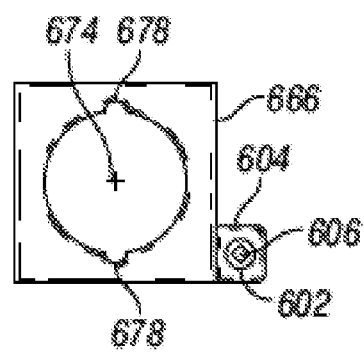

FIG. 9 is a diagrammatic elevational view depicting certain components of a system according to yet another embodiment of the invention.

DETAILED DESCRIPTION

A system according to one embodiment of the invention includes an anchor ring assembly 10 depicted in FIG. 1. The anchor ring assembly includes an anchor ring 12. Anchor ring 12 includes a generally hoop-like metallic body 14. Body 14 has a flange 16 at a distal end, a generally cylindrical exterior surface 18 projecting in the proximal direction P from flange 16, and a further small flange 20 projecting outwardly from the exterior surface at the proximal end of the anchor ring. The anchor ring is hollow and has a generally spherical interior surface (not shown). The anchor ring has a slot 22 extending through it at one location on its circumference. The slot allows the anchor ring to be compressed slightly so as to reduce its diameter and thus reduce the interior diameter of the spherical interior surface. Anchor ring 12 is intended to be fastened to the exterior of the heart during use. For this purpose, the anchor ring is provided with a fabric ring 24 attached to flange 16. The anchor ring can be secured to the exterior surface of the heart by stitching the fabric ring to the heart in a conventional manner.

Other structures that are capable of anchoring the anchor ring to the wall of the heart may be used instead. For example, as disclosed in U.S. Provisional Patent Application No. 61/894,117, the disclosure of which is incorporated by reference herein, the anchor ring may be provided with metallic anchoring elements that penetrate into the heart muscle so as to secure the anchor ring in place on the exterior surface of the heart.

Anchor ring 12 further includes a gimbal element 26 mounted inside anchor ring 14. The gimbal element 26 has a spherical exterior surface 28 engaged with the spherical interior surface of the anchor ring. Gimbal element 26 is also hollow and defines an interior bore 30 extending in the proximal direction P and distal direction D. The spherical exterior surface of the gimbal element allows the gimbal element to tilt slightly relative to the anchor ring. Gimbal element 26 also has a slot 32 extending through it at one point on its circumference. Thus, when anchor ring 12 is compressed as discussed above, gimbal element 26 will also be compressed so as to reduce the diameter of bore 30.

The anchor ring 12 further includes a clamp ring 34 extending around the exterior of the cylindrical surface 18 of the anchor ring. The claim ring 34 is engaged between the distal flange 16 and the proximal flange 20. Clamp ring 34 has a pair of diametrically opposed cut-outs 39, only one of which is visible in FIG. 1. Clamp ring 34 also has a slot (not shown) extending through it at one point on its circumference. A pair of clamp arms 36 project outwardly from the clamp ring on opposite sides of the slot. A link 38 is pivotally mounted to one of the arms 36 and projects across the slot to the opposite arm 36. A screw 40 is threadedly engaged with one of the arms. The axis of the screw extends generally in the proximal and distal directions, with the head of the screw facing in the proximal direction. The screw has a generally conical cam surface 42 facing in the distal direction. By engaging a tool in the head of screw 40 and rotating the screw, the cam surface 42 can be forced in the distal direction so that it engages link 38 and pulls the arms 36 closer to one another. This action tightens the clamp ring 34 and thus constricts the anchor ring 14 and the gimbal element 26, thereby reducing the diameter of bore 30.

The anchor ring assembly further includes a valve 40. Valve 40 includes a valve housing formed by a pair of valve housing elements 42*a* and 42*b*. Each housing element includes a proximal section 44 and a distal section 46. The proximal and distal sections of each housing element 42 are permanently fastened to one another. The proximal section 44 of each housing element has a generally semicircular wall 48 projecting in the proximal direction. Each wall 48 has lips 61 projecting outwardly from the wall and extending in the proximal-to-distal direction.

The distal section 46 of each housing element has a recess 52. Each housing element also has a catch 50 that projects slightly from the surface of the recess.

Housing element 42*a* has a pair of pins 54, of which one is visible in FIG. 1, whereas the opposite housing element 42*b* has a pair of holes 56. The housing elements can be releasably secured to one another by engaging pins 54 in holes 56. Housing element 42*a* has a hole 58 extending through its semicircular wall 48. As shown in FIG. 2, housing elements 42*a* and 42*b*, when engaged with one another, cooperatively define a bore 60. The housing elements can be secured to anchor ring 12 in the assembled condition shown in FIG. 2 by assembling the housing elements to one another and engaging the catch element 50 in one of the cut-outs 39 in the clamp ring. (FIG. 1.) In this condition, the catch elements 50 are engaged under the proximal flange 20 of the anchor ring body so that the assembled housing elements are locked to the anchor ring. In this condition, the bore 60 defined by the assembled valve housing elements constitutes a continuation of the bore 30 extending through anchor ring 12.

Valve elements 62*a* and 62*b* are slidably mounted to valve housing elements 42*a* and 42*b* respectively. The valve elements are slidable between the closed position depicted in solid lines in FIG. 1 and an open position partially depicted in broken lines at 62*a*' and 62*b*'. In moving from the closed position to the open position, the valve elements travel in directions transverse to the proximal-to-distal directions and transverse to the axis 63 (FIGS. 1, 2) of the combined bore defined by the valve housing elements and anchor ring. When the valve elements are in the closed position, they substantially abut one another and substantially occlude the bore. Valve element 62*a* has a hole 64 in the end of the valve element facing away from the axis of the bore. Valve element 62*b* has a similar hole (not shown).

The system further includes a preparation tool and coring device shown in FIGS. 2, 3, and 4. The preparation tool includes a preparation tool body 66 having a proximal end 68, a distal end 70, and a cylindrical passage 72 extending between the proximal and distal ends and defining a proximal-to-distal axis 74. Passage 72 has an enlarged section 76 (FIG. 4) at its distal end. As best seen in FIG. 5, body 66 has a pair of keyways 78 extending proximally-to-distally within the enlarged section 76 of passage 72.

A groove 80 extends proximally-to-distally on the exterior surface of body 66. Body 66 also has a pair of grooves 82 extending transverse to the axis 74 on one surface of the housing. These grooves are spaced apart from one another in the proximal-to-distal direction. Body 66 also has a pair of pockets 84 formed on opposite surfaces of the body at the distal end 70. The body further has a proximal stop hole 86a and a distal stop hole 86b extending into the body from one surface.

The preparation tool further includes a catch lever 90 having a projection 92 at one end and a handle 94 at the opposite end. The catch lever 90 is pivotably mounted to body 66 by a pivot pin 98, so that the handle 94 is disposed adjacent the proximal end 68 of body 66. The catch lever is movable between an engaged position and a disengaged position. The engaged position is depicted schematically in FIG. 5. In this engaged position, projection 92 extends into the enlarged portion 76 of the passageway through a hole (not shown) in body 66. In the disengaged position, projection 92 is retracted out of the enlarged portion 76 of the passageway. A biasing element biases the catch arm toward the engaged position. The biasing element may be a spring schematically represented at 98 in FIG. 2.

The preparation tool further includes a pair of valve actuating elements 100. The valve actuating elements have pins 102 projecting from their distal ends. The valve actuating elements 100 also have guide pin holes 104 remote from their distal ends. A set of guide pins 106 are received in the guide pin holes 104 of the valve actuating elements. The guide pins are also received in the slots 82, best seen in FIG. 3). As best seen in FIG. 4, the proximal portions of valve actuating elements 100 overlie the surface of body 66 bearing slots 82.

A slide plate 110 has central slots 112 extending through it. The central slots extend in the proximal-to-distal direction. The slide plate also has pairs of oblique slots 114 extending through it. The oblique slots are oblique to the proximal-to-distal direction of the slide plate and converge with one another in the distal direction. Slide plate 110 also has an operating hole 116 at its proximal end. Slide plate 110 overlies the proximal portions of valve actuating elements 100, so that the proximal portions of the valve actuating elements are sandwiched between the slide plate and body 66. The guide pins 106 associated with the valve actuating elements are engaged in the oblique slots 114 of the slide plate.

A cover plate 120 overlies the slide plate 110. The cover plate is fixed to body 66 by bolts (not shown). Cover plate 122 has a pair of bosses 122 projecting from it. These bosses are engaged in the central slots 112 of slide plate 110. Thus, slide plate 110 is constrained to move relative to housing 66 only in the proximal-to-distal direction. Valve actuating elements 100 are constrained by pins 106 and slots 82 to move only in directions T transverse to the proximal-to-distal direction.

As depicted in FIGS. 4 and 5, the slide plate 110 is in a fully retracted position, at the proximal limit of its travel. In this condition, valve actuating elements 100 and hence pins 102 projecting from the distal ends of the valve actuating elements are close to one another and relatively close to the central axis 74 of the passageway in body 66. An operator can grasp slide plate 110 by its proximal end as, for example, by grasping the slide plate at operating hole 116 and move the slide plate in the distal direction. Upon such movement, the engagement between the guide pins 106 (FIGS. 2 and 3) and the oblique slots 114 forces the guide pins and hence valve actuating elements 100 to move away from one another in the transverse direction T. The engagement between the guide pins 106 and slots 82 in the body 66 prevents the valve actuating elements and guide pins from moving distally with the slide plate. Thus, distal motion of the slide plate causes the valve actuating elements 100 to move away from one another, to the open position indicated in broken lines at 100' in FIG. 5. Moving the slide plate proximally relative to the housing causes the valve actuating elements 100 to move towards one another, back to the closed position indicated solid lines in FIG. 5.

The system according to this embodiment of the invention further includes a coring tool. The coring tool includes a tubular housing 130. A handle 132 is fixed to the housing 130 at the proximal end thereof. A generally cylindrical anvil 134 is fixed to housing 130 at the distal end of the housing. Anvil 134 defines a cutting surface 136 facing in the distal direction and forming the distal end of the housing 130. Handle 132 and anvil 134 have holes 138 and 140 extending through them in the proximal-to-distal direction. These holes are coaxial with the cylindrical exterior surface of housing 130

A shaft 144 is slidably received in holes 138 and 140. A coring element 146 is fixed to the distal end of shaft 144. Coring element 146 is generally in the form of a hollow cylindrical shell with a conical exterior surface 147 at its distal end. The coring element has a sharp, circular edge at its proximal end. An operating knob 150 is fixed to shaft 144 at its proximal end. A ring 152 is secured to shaft 144. A compression spring 154 surrounds shaft 144, and is engaged between ring 152 and anvil 134. Spring 154 normally keeps shaft 144 and coring element 146 in the retracted position shown. In this retracted position, coring element 146 is engaged with surface 136 at the distal end of housing 130. However, an operator can move the shaft and coring element in the distal direction relative to the housing by displacing actuating knob 150 distally.

A stop lever 160 is pivotally mounted to the handle 132 of the coring device. Stop lever 160 has an enlarged head 162 at its distal end and a stop pin 164 projecting from the head. As best appreciated with reference to FIG. 4, an operator can swing head 162 away from the housing 130 of the coring tool by forcing the proximal end of lever 160 towards shaft 144. A spring 166 schematically indicated in FIGS. 2 and 4 biases the distal portion of the lever and head 162 toward the housing 130.

As shown in FIG. 4, the housing 130 of the coring tool is slidably received within the passage 72 of the body 66 of the preparation tool. Desirably, the exterior diameter of housing 130 forms a close but slidable fit with the inside diameter of passage 72. As depicted in FIG. 4, the coring tool is in a storage position. In this position, the stop pin 164 of the stop actuation lever 160 is engaged in proximal stop hole 86a and the coring tool does not extend distally beyond the body 66.

The preparation tool can be engaged with the anchor ring assembly 10. The slide plate 116 is to bring the valve actuating elements 100 to the closed position depicted in FIG. 5. Catch lever 90 is moved to the disengaged position to retract projection 92 out of the enlarged portion 76 of the passage. With the preparation tool in this condition, and with the valve elements 62a and 62b in the closed position shown in solid lines in FIG. 1, the distal end of the coring tool can be placed over the tubular structure formed by walls 48 forming the proximal end of the valve housing. The preparation tool can be rotated about its axis 74 so as to bring keyways 78 (FIG. 5) into alignment with the lips 61 of the valve. As the preparation tool body 66 is advanced distally toward the anchor ring assembly 10, the pins 102 on the valve actuating elements enter into the holes 64 (FIG. 1) on the valve elements. At the same time, the tubular structure formed by the proximal projecting walls 48 of the valve body is telescopically received within the enlarged section 76 of the passage in preparation tool body 66. The lips 61 act as keys and enter into the keyways 78 in the enlarged portion of the passageway (FIG. 5). This keying action assures that the valve body of the anchor ring assembly is in a predetermined alignment with the features of the anchor ring assembly. Thus, the pins 102 of the valve actuating elements will be aligned with the holes 64 of the valve element. Also, hole 58 on the valve body (FIG. 1) is aligned with the projection 92 of latch 90. Once the valve body has been fully seated into the enlarged section 72 of the passage, the operator releases the latch lever 90 and thus the projection 92 enters into hole 58. This locks the entire anchor ring assembly in a predetermined position relative to the body 66 in the proximal and distal directions.

With the preparation tool body 66 locked to the anchor ring assembly in this manner, the bore defined by the anchor ring assembly, including the bore 60 of the valve assembly and the bore 30 of the anchor ring, is continuous with the passage 72 in the preparation tool body 66. The valve elements 62 can be moved to their open position by an operator grasping slide plate 110 as by engagement feature 116 and moving the slide plate in the distal direction. This moves the valve operating elements 100 outwardly. The pins 102 on the valve elements move the valve elements outwardly to the open position. When the valve elements are in their open position, the bore of the anchor ring assembly is substantially unoccluded. The operator can bring the valve elements back to their closed position by moving the slide in the proximal direction. In the closed position, the valve elements 62 substantially occlude the bore in the anchor ring assembly.

Typically, the coring tool is engaged in the preparation tool body before the preparation tool body is engaged with the anchor ring assembly. Ordinarily, when the coring tool body is first engaged with the anchor ring assembly, the coring tool is in the storage position depicted in FIG. 4, with the stop pin 162 engaged in the proximal stop hole 86a. As further discussed below, the coring tool is brought to an advanced position to core the muscle of the heart. To move the coring tool to the advanced position, the operator moves the valve elements to the open position as discussed above and actuates the stop lever 160 to disengage the stop pin from the proximal stop hole 86a. The operator can then slide the coring tool housing 130 distally within the passage 72 of the coring tool body until the stop pin 162 engages the distal stop hole 86b under the influence of spring 166. This stops the coring tool at the advanced position. In this advanced position, the cutting surface 136 forming the distal end of the coring tool body is aligned with the distal side of anchor ring 14, and the coring element 146 projects distally beyond the anchor ring. The coring tool can be moved back to the storage position by reversing these steps.

The system according to this embodiment of the invention desirably further includes an installation tool 200 depicted in FIG. 6. Installation tool 200 has a body 266 with a proximal end 268, a distal end 270, and a passage 272 extending between the proximal and distal ends of the body. Body 266 also has a slot 202 extending entirely through one wall and extending from the proximal end of the body to the distal end. Slot 202 communicates with passage 272. The walls of slot 202 define a pair of grooves 204, of which one is visible in FIG. 6.

Passage 272 has an enlarged section (not shown) at its distal end, identical to the enlarged section 76 of the preparation tool body (FIG. 5). The enlarged section is provided with key slots similar to slots 78 discussed above with reference to FIG. 5 and also has a latch opening similar to the corresponding feature of the preparation tool body discussed above. In this embodiment, the installation tool body 266 is longer in the proximal-to-distal direction than the preparation tool body 66 discussed above. The other features of the installation tool body 266 may be identical to the corresponding features of the preparation tool body.

The installation tool further includes a closure element 206 formed from a resilient, liquid-impervious material such as a rubber or a rubber-like polymer. The closure element is in the form of an elongated strip having an inner surface 208 and ridges 210 projecting from side surfaces remote from the inner surface. Inner surface 208 is in the form of fragment of a cylindrical surface having radius equal to the radius of the cylindrical passageway 272 in the installation tool body. The closure element or strip 206 is normally positioned in slot 202 with ridges 210 received in the grooves 204 of the slot. In this position, the inner surface 208 is substantially continuous with the inner surface of passage 272 and the strip substantially closes slot 202.

While the closure element 206 is in place within slot 202, it seals the slot so that the walls of body 266 bounding passageway 272 between its proximal and distal ends are substantially fluid-tight. However, closure element 206 can be dislodged progressively along the length or proximal-to-distal extent of body 266 so as to progressively open slot 202 along the length of the body. Thus, closure element 206 serves as a means for progressively forming an opening in installation tool body 266 along its length.

The installation tool 200 further includes valve actuating elements 220, a slide plate 230, and a cover 240. These elements are identical to the corresponding valve actuating elements 100, slide plate 110, and cover 120 of the preparation tool discussed above. The valve actuating elements 220, slide plate 230, and cover 240 are mounted to the installation tool body 266 in exactly the same manner as the corresponding components of the preparation tool and function in the same way. Likewise, a latch lever 290 is mounted to insertion tool body 266 in the same manner as the latch lever 90 discussed above with reference to the preparation tool.

The insertion tool can interact with and engage the anchor ring assembly, including the valve body and the valve elements in exactly the same manner as the preparation tool discussed above. For example, when the distal end 270 of the insertion tool valve body is engaged with the anchor ring assembly 10, the anchor ring assembly, and specifically the generally cylindrical wall 48 defined by the valve body (FIGS. 1 and 2), is telescopically received within the enlarged section of the passageway 272 in the insertion tool body 266. The latch on lever 290 is engaged in the hole 58 in the cylindrical wall of the valve body, so that the anchor ring assembly is locked in place relative to the installation tool body. Here again, the bore in the anchor ring assembly communicates with the passage 272 in the installation tool body. Also, the valve actuating elements 220 are engaged with the valve elements 62 of the anchor ring assembly by means of the pins 222, one of which is visible in FIG. 6, carried by the valve actuating elements. In exactly the same manner as discussed above with reference to the preparation tool, the operator can actuate the slide element 230, as by engaging the engagement hole 216 at the proximal end of the slide to move the valve elements 220 from their closed position to the open position.

A VAD 300 (FIG. 6) used with the tools discussed above may be generally as disclosed in the aforementioned U.S. Patent Application Publication No. 2009/0203957. The VAD includes a pump body 302 and internal components such as an impeller (not shown) and electrical coils for moving the impeller within the pump body 302. The pump body 302 defines an inlet 304 at its proximal end. An outlet tube 306 communicates with the pump body and projects distally from the pump body. The outlet tube has outlet apertures 308 at its distal end. The VAD further includes a cylindrical base body 310. Base body 310 may have a passageway 312 schematically indicated in FIG. 6 extending through the base body from its proximal end 314 to its distal end 316. Passageway 312 is closed by a removable closure 318 at the proximal end of the base body. A projection 320 extends from the base body in a direction transverse to the axis of the base body and thus transverse to the proximal and distal directions. An electrical cable 322 is connected to the base body by means of projection 320. A strut 324 mechanically connects the base body 310 and pump body 302. Electrical conductors from cable 322 extend through the base body and through strut 324 to the pump body.

Cable 322 may be connected to a controller (not shown) mountable within the body. Alternatively, cable 322 may extend to a skin-penetrating electrical connection, which in turn is connected to an external controller. In yet another alternative, cable 322 may be arranged to extend through the skin of the patient when the VAD is mounted in the patient's body.

In a pump implantation method according to one embodiment of the invention, the surgeon makes an incision in the patient's chest so as to expose the apex of the heart. The incision may be relatively small as, for example, about 5 cm in diameter. The surgeon then attaches the anchor ring 12 (FIG. 1) to the wall of the heart adjacent the apex of the heart. At this time, the clamp of the anchor ring is open, so that the clamp ring 34 is relaxed and the anchor ring 12 and gimbal 30 are not compressed. The anchor ring is attached with the distal surface (the surface facing downwardly in FIG. 1) abutting the wall of the heart and with the proximal flange 20 of the anchor ring facing away from the heart. The surgeon may make a small starting incision through the wall of the heart inside the bore 30 of the anchor ring. The incision may be, for example, in the form of two cuts crossing one another to form an x-shape. With the small incision, some blood will leak from the heart as the heart continues to beat. However, such blood loss will not be so substantial as to be immediately life-threatening.

The surgeon then assembles the valve to the anchor ring by assembling the valve housing elements 42a and 42b with one another and engaging the projections 50 (FIG. 1) under the proximal flange 20 of the anchor ring. Desirably, the valve elements 62a and 62b are in their closed positions when the valve elements are assembled with one another. Once the valve elements have been assembled with one another, the valve elements substantially occlude the bore 30 in the anchor ring. In a variant of this procedure, the surgeon may assemble the valve housing elements 42a and 42b with one another and engage the same with the proximal flange of the anchor ring before making the incision, and may manually bring the valve elements 62a and 62b to their open position. In this condition, the surgeon can make the incision through the bore 60 (FIG. 2) in the valve body and through the bore 30 of the anchor ring. After making the incision, the surgeon may manually move the valve elements back to their closed positions so as to substantially occlude the bore in the anchor ring assembly.

The valve elements in their closed position need not form a perfect seal. Some seepage of blood may occur even when the valve elements are closed. However, the valve elements in their closed position occlude the bore sufficiently to avoid any gross loss of blood that would be immediately threatening to the patient.

With the valve in place on the anchor ring and the valve elements in the closed position, the surgeon engages the preparation tool (FIGS. 2, 3, and 4) with the anchor ring assembly in the manner described above. At this time, the coring tool is desirably in place within the passage 72 of the preparation tool. The surgeon then manipulates the slide plate 110, as by grasping engagement hole 116 and forcing the slide plate distally, so as to bring the valve elements to their open position. The surgeon can do this readily, because the engagement hole 116 in the slide plate is remote from the distal end of the preparation tool body and remote from the heart. For example, the engagement hole 116 may protrude out of the patient's body or may be within the incision close to the surface of the patient's body. With the valve elements in the open position, some blood will flow into the distal end of the passageway in the preparation tool body. However, the housing 130 of the coring tool substantially occludes the passageway and prevents gross loss of blood.

With the valve elements in the open position, the housing of the coring tool is advanced distally by manipulating handle 132. The pointed end of coring element 146 enters the heart and forces tissue aside. The distal travel of the coring tool housing and coring element is arrested when the distal end 162 of the stop lever 160 becomes aligned with the distal stop hole 86b in the coring tool body (FIGS. 2 and 4), so that the stop pin 164 on the stop lever engages the distal stop hole 86b. In this condition, the cutting surface 136 on the distal end of the coring tool housing is aligned with the distal surface of the anchor ring 12 and thus aligned with the exterior surface of the heart wall.

The surgeon then actuates the coring tool by forcing operating knob 150, and hence shaft 144 and coring element 146, distally relative to the coring tool housing and hence relative to the anchor ring and preparation tool body. The displaced tissue becomes engaged between the cutting edge 148 (FIG. 2) of the coring element 146 and the cutting surface 136 at the distal end of the coring tool housing. The surgeon then retracts actuating knob 150 and hence the coring element proximally, so that the engaged tissue is cut by the cutting edge and captured inside the hollow coring element 146. This forms a hole in the wall of the heart having a diameter just slightly less than or equal to the diameter of the bore in the anchor ring assembly. Typically, this diameter is about 18 millimeters. However, because the housing 130 of the coring tool continues to substantially occlude the passage 72 in the preparation tool body, there is only minimal blood seepage from the heart. The coring tool is then retracted to the retracted position depicted in FIG. 4 by pulling handle 132 proximally.

The surgeon then actuates the slide plate to move the valve actuating elements 100 and the valve elements 62 to their closed position. With the valve elements in the closed position, the surgeon then actuates the latch lever 90 of the preparation tool to release the preparation tool from the anchor ring assembly and withdraws the preparation tool and coring tool from the patient's body. At this time, the bore in the anchor ring assembly is again substantially occluded by the valve elements 62 so that there is no massive blood loss but, at most, some blood seepage.

The surgeon positions the VAD within the passage 272 of the insertion tool 200 (FIG. 6). At this stage, the closure element 206 is disposed in slot 202. The VAD is positioned in the passageway of the installation tool so that the proximal end 314 of the base body 310 projects out of the proximal end 268 of the installation tool body. The remainder of the base body, including the distal end 316, is disposed within passage 272 and substantially occludes the passage. The projection 320 on the base body is aligned with slot 204. The distal end of the outlet cannula 306 is disposed adjacent the distal end of the installation tool body 266. The surgeon then engages the distal end 270 of the installation tool with the anchor ring assembly, so that the latch on the latch lever 290 (FIG. 6) is engaged with the hole 58 in the valve housing of the anchor ring assembly. The valve elements 62 of the anchor ring assembly remain closed. In this condition, the valve elements 62 substantially occlude passageway 272 and separate the passageway from the bore 30 in the anchor ring. Stated another way, the passageway 272 is substantially occluded at both ends by the base body 310 of the VAD and by the valve elements.

At this stage, the space within the passageway surrounding the VAD as, for example, the space between the base body 310 and pump body 302 and the space surrounding the outflow cannula 306 may be full of air. Likewise, the space inside pump body 302 and outflow cannula 306 also may be filled with air. The surgeon may remove closure 318 of the base body (FIG. 6) and insert a cannula (not shown) through the passage 312 in the base body. The surgeon may insert a liquid such as saline solution through the passageway so as to flush the space within the passageway 272 of the installation tool body and the space within the pump and outflow cannula. Alternatively, the surgeon may remove closure 318 and briefly open the valve elements 62 by actuating the slide 220 of the installation tool so that blood advances into the space within passageway 272 and the space inside the pump. As the blood advances, air is forced out through the passage 312 in the base body. When the base has been purged in this manner, a small amount of blood will begin to leak from the assembly through the passageway 312 in the base body. The surgeon may then reinstall the closure 318.

With the valve elements in the open position, the surgeon advances the VAD distally within passageway 272. As the surgeon advances the VAD, the VAD passes through the anchor ring and into the heart. As the VAD moves distally, projection 320 passes into slot 202. The surgeon progressively peels closure element 206 out of the slot so as to allow the projection 320 to pass distally within the slot as the VAD advances. During this stage, however, the slot remains substantially sealed by the closure element at all locations distal to the distal end 316 of the base body 310. Thus, the space within the passageway 272 distal to the base body, as well as the space within the VAD itself, remains substantially full of liquid. As the VAD advances, the outflow tube 306 of the VAD is advanced through the ventricle of the patient's heart and into an artery as, for example, into the aorta. At the same time, the pump body 302 is advanced through the bore in the anchor ring assembly and into the ventricle. This action continues until the base body 310 is engaged in the bore 30 of the anchor ring.

At this time, the clamp of the anchor ring is actuated, as by turning screw 40 using a screw driver (not shown) passed along the outside of the installation tool. The clamp is actuated to compress the anchor ring 12 and the gimbal 30, thereby locking the base body 312 into the anchor ring and plugging the anchor ring. The surgeon then actuates latch lever 290 to release the installation tool and slides the installation tool proximally away from the anchor assembly, leaving the VAD in place. As the surgeon moves the installation tool in this manner, the projection 320 exits through the distal end of slot 204.

The surgeon may then remove the valve body from the anchor ring by manually pulling the valve housing elements 42a and 42b away from one another, thereby releasing the valve housing elements from the anchor ring. At this juncture, installation of the VAD within the heart is complete. The VAD may be started and operated in the normal manner to assist the patient's circulation.

Numerous variations and combinations of the features discussed above can be utilized without departing from the present invention. For example, the installation tool described above with reference to FIG. 6 can also be used as the preparation tool. That is, the coring device can be introduced through the passage 272 of the installation tool and then removed after formation of the hole in the heart wall and closure of the valve elements. After removal of the coring device, the VAD can be introduced into the passage of the installation tool. The installation tool may be provided with stops such as the stop holes 86a, 86b (FIGS. 2 and 4) used to control the motion of the coring device housing as discussed above. The stops used to control motion of the coring device can be varied. For example, a stop may be provided at the proximal end of the preparation tool housing to engage the handle 132 of the coring device and thus arrest motion of the coring device housing at the retracted position shown in FIG. 4. The stop may be removable to permit advancement of the coring device. The handle may be arranged to engage the proximal end of the preparation tool body when the coring device housing is in the advanced position, with the distal end of the coring device coplanar with the distal surface of the anchor ring.

In the embodiments discussed above, the valve elements are slidably mounted to the valve body for sliding motion between their open and closed positions. However, in other variants, the valve elements may be arranged to swing about pivots on the valve housing so as to open and close. In the embodiments discussed above, two valve elements are employed. However, more than two valve elements, or only one valve element, can be used, provided that the valve element or valve elements substantially occlude the bore when the same are in their closed position. The valve elements should be substantially clear of the bore when they are in their open position, so that the valve elements do not substantially obstruct the bore in the open position.

In the arrangements discussed above, the proximal end of the slide plate 110 and the engagement hole 116 at the proximal end of the slide plate serve as a control element, which the surgeon or other operator may grasp and manually operate to move the valve elements. This control element is mechanically linked to the valve actuating elements by the slide plate itself and the guide pins, so that the valve actuating elements can be moved between their open and closed positions by moving the control element. However, other forms of mechanical linkage between the control element and the valve actuating elements can be employed. For example, any arrangement of cams, levers, gears, belts, pulleys, or other mechanical elements that are operative to move the valve actuating elements responsive to operation of the control element can be employed. The linkage between the control element and the valve actuating elements need not be mechanical. Pneumatic, hydraulic, or electromechanical elements such as motors and solenoids can be used to drive the valve actuating elements responsive to actuation of the control element.

Further, in the embodiments discussed above, the valve actuating elements are directly linked to the valve elements by the pins on the valve actuating elements when the tool is coupled to the anchor ring assembly. However, the valve actuating elements may be indirectly linked to the valve elements by components incorporated in the anchor ring assembly as, for example, by operating handles or linkages included in the valve itself.

In the embodiments discussed above, the valve is detachable from the anchor ring so that the valve can be removed from the patient after installation of the VAD. In other embodiments, however, the valve may be permanently attached to the anchor ring. In still other embodiments, the valve may be formed with a unitary housing that is attachable to the anchor ring and detachable from the anchor ring by structures such as threads or a bayonet lock.

In the embodiments discussed above, the removable closure element 206 (FIG. 6) serves to form an opening in the wall of the installation tool housing, which opening progresses in the proximal-to-distal direction. However, other structures that can accomplish this function may be used. For example, as schematically depicted in FIG. 7, the installation tool body 466 may be provided with a pair of resilient lips 402 that cooperatively close a slot 404 in the body communicating with the passage 472 of the body. The resilient lips are arranged so that as the projection 420 on the base body 410 of the VAD moves distally, the projection displaces the resilient lips in the immediate vicinity of the projection to form an opening 401. The opening 401 travels progressively in the distal direction D as the VAD continues to move in the distal direction.

In a further arrangement schematically depicted in FIG. 8, the installation tool body 566 has a similar slot 504. The slot 504 is covered by a plate 501 having an edge 503 oblique to the proximal and distal directions. Plate 501 is slidably or pivotally mounted to body 566 for movement of the plate in a direction generally transverse to the proximal and distal directions. The plate is also arranged to bear against the surface of the housing and seal slot 504 in regions covered by the plate. As the projection 520 on the VAD 510 moves distally, the plate is displaced in the transverse direction T, thus uncovering slot 504 progressively in the distal direction and forming the progressively advancing opening.

In still other embodiments, where the VAD does not incorporate a projection extending in directions transverse to its axis, the arrangement for performing the advancing opening in the wall of the installation tool may be omitted.

As discussed above with reference to FIGS. 1 and 5, the anchor ring assembly includes a locking mechanism actuating by turning a screw 40. When the preparation tool or installation tool is engaged with the anchor ring assembly, the anchor ring assembly lies in a predetermined rotational position around the axis of the passage in the tool as, for example, in a predetermined orientation around axis 674 (FIG. 9) maintained by engagement between the lips 61 of the valve housing and the slots 678 in the distal end of the tool. As schematically depicted in FIG. 9, the preparation or installation tool body 666 may be provided with features such as an auxiliary passage 602 formed in the body or in a structure 604 attached to the body extending proximally and distally. This passage 602 lies at a predetermined position relative to the features 678 of the body 666 that align the anchor ring assembly with the tool body. The position of auxiliary passage 602 is selected so that when the anchor ring assembly is engaged with the anchor ring assembly, passage 602 will be aligned with the head of the screw 40 (FIG. 1) that actuates the clamp. A tool 606, such as a screw driver, may be advanced through the auxiliary passageway to the screw 40 on the clamp. The tool body thus serves to guide the driver and facilitate engagement of the driver with the actuating feature of the clamp. Similar arrangements can be used where the clamp incorporates features other than a screw.

As these and other variations and combinations of the features described above can be employed, the foregoing description of certain embodiments should be taken as illustrating rather than as limiting the present invention. Certain aspects of the present invention are further described by the numbered paragraphs set forth below.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for installation of a ventricular assist device comprising:
   (a) an anchor ring assembly including an anchor ring adapted for fastening to the wall of the heart, the anchor ring assembly defining a bore having proximal and distal ends, the distal end of the bore facing toward the wall of the heart when the anchor ring is fastened to the wall of the heart, the anchor ring assembly further including at least one or more valve elements movable between a closed position in which the one or more valve elements substantially occlude the bore and an open position in which the one or more valve elements do not substantially occlude the bore; and
   (b) at least one tool, each said tool including:
      (i) a tool body having proximal and distal ends, a proximal-to-distal axis extending therebetween, and a passage extending between the ends of the body along the proximal to distal axis, the distal end of the body being adapted to releasably engage the anchor ring assembly so that the passage communicates with the bore;
      (ii) one or more valve actuating elements movably mounted to the body, the valve actuating elements being mechanically linked to the valve elements when the body is engaged with the anchor ring assembly to open and close the valve elements; and
      (iii) a control element operatively connected to the valve actuating elements so as to control the valve actuating elements to move the valve elements between the open and closed positions by actuating the control element, at least a part of the control element being disposed remote from the distal end of the body.

2. A system as claimed in claim 1 wherein, in each said tool, the valve actuating elements include distal portions disposed adjacent the distal end of the body and the distal portions are movable in directions transverse to the proximal-to-distal axis.

3. A system as claimed in claim 2 wherein, in each said tool, the distal portions of the valve actuating elements include pins projecting in the distal direction of the tool body, and wherein the valve elements of the anchor ring assembly include holes, the pins being engaged in the holes when the tool is engaged with the anchor ring assembly.

4. A system as claimed in claim 2 wherein, in each said tool, the distal portions of the valve actuating elements are movable in directions towards and away from the proximal-to-distal axis.

5. A system as claimed in claim 1 wherein the control element of each said tool is movably mounted to the body.

6. A system as claimed in claim 5 wherein each said tool includes a mechanical linkage operatively connecting the control element and the valve actuating elements.

7. A system as claimed in claim 5 wherein the control element of each said tool is movable relative to the body in the proximal and distal directions.

8. A system as claimed in claim 1 wherein the anchor ring assembly includes a valve housing releasably connectable to the anchor ring, the valve elements being movably mounted to the valve housing.

9. A system as claimed in claim 8 wherein the valve housing defines the proximal end of the bore and the anchor ring defines the distal end of the bore when the valve housing is connected to the anchor ring.

10. A system as claimed in claim 9 wherein the valve housing is adapted to telescopically engage the body of each said engagement tool.

11. A system as claimed in claim 9 wherein the valve housing includes a plurality of valve housing elements which are releasably engagable with one another, the valve housing elements cooperatively defining the proximal end of the bore when engaged with one another and connected to the anchor ring.

12. A system as claimed in claim 1 wherein the at least one tool includes an installation tool and wherein the tool body of the installation tool includes a major portion having a slot extending between the proximal and distal ends of the body and a closure element releasably received in the slot.

13. A system as claimed in claim 12 further comprising a ventricular assist device adapted for insertion into the heart of a patient through the passage of the installation tool and the bore of the anchor ring assembly, the ventricular assist device including a cable adapted to pass through the slot of the installation tool body when the closure element is not received in the slot.

14. A system as claimed in claim 1 wherein the at least one tool includes a preparation tool, the system further comprising a cutting device adapted to be received in the passage of the preparation tool body and to engage the wall of the heart through the bore of the valve assembly.

15. A system as claimed in claim 14 wherein the cutting device is a coring device having a housing with proximal and distal ends, a coring element movably mounted to the housing and wherein the housing of the coring device is adapted to be slidably received in the passage of the preparation tool body.

16. A system as claimed in claim 15 wherein the preparation tool includes a first stop adapted to releasably hold the housing of the coring device in a first position so that the coring element will be proximal to the valve elements when the coring element is in the retracted position.

17. A system as claimed in claim 16 wherein the anchor ring has a distal surface adapted to bear on the wall of the heart and the preparation tool includes a second stop adapted to releasably hold the housing of the coring device in an advanced position wherein the distal end of the housing of the coring device is aligned with the distal surface of the anchor ring, and wherein the coring element is mounted to the housing for movement relative to the housing in a distal direction from a retracted position in which the coring element is engaged with the housing and an extended position in which the coring element is remote from the housing.

* * * * *